(12) United States Patent
Ware et al.

(10) Patent No.: US 9,005,150 B2
(45) Date of Patent: Apr. 14, 2015

(54) FLOW BALANCING SYSTEM AND METHOD, ESPECIALLY FOR CITRATE

(75) Inventors: Lee C. Ware, Chicago, IL (US); Arnold F. Boehnlein, Clearwater, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 799 days.

(21) Appl. No.: 13/185,147

(22) Filed: Jul. 18, 2011

(65) Prior Publication Data

US 2011/0266221 A1 Nov. 3, 2011

Related U.S. Application Data

(60) Continuation of application No. 12/763,864, filed on Apr. 20, 2010, now Pat. No. 8,317,750, which is a division of application No. 11/356,661, filed on Feb. 16, 2006, now Pat. No. 7,699,806, which is a division of application No. 10/685,724, filed on Oct. 15, 2003, now Pat. No. 7,029,456.

(51) Int. Cl.
| | | |
|---|---|---|
| *A61M 37/00* | (2006.01) | |
| *A61M 1/34* | (2006.01) | |
| *A61M 5/142* | (2006.01) | |
| *G06F 19/00* | (2011.01) | |
| *A61M 5/168* | (2006.01) | |

(52) U.S. Cl.
CPC ............ *A61M 1/3441* (2013.01); *A61M 5/142* (2013.01); *A61M 5/16827* (2013.01); *A61M 2005/14208* (2013.01); *G06F 19/3468* (2013.01)

(58) Field of Classification Search
CPC ... A61M 1/16; A61M 1/3639; A61M 1/3621; A61M 1/1037; A61M 1/101; A61M 1/3627; A61M 1/34; A61M 1/3693
USPC ............................ 604/4.01–6.16, 65–67, 131
See application file for complete search history.

(56) References Cited

U.S. PATENT DOCUMENTS

| | | | | |
|---|---|---|---|---|
| 3,807,401 A | * | 4/1974 | Riggle et al. | 604/269 |
| 4,258,723 A | * | 3/1981 | McCue et al. | 600/580 |
| 4,275,726 A | | 6/1981 | Schael | |
| 4,500,309 A | | 2/1985 | Diederich et al. | |
| 4,661,246 A | | 4/1987 | Ash | |
| 4,713,176 A | * | 12/1987 | Schoendorfer et al. | 210/645 |
| 4,747,950 A | | 5/1988 | Guinn | |
| 4,898,578 A | | 2/1990 | Rubalcaba | |
| 4,968,295 A | * | 11/1990 | Neumann | 604/6.07 |
| 4,995,268 A | | 2/1991 | Ash et al. | |
| 5,011,607 A | | 4/1991 | Shinzato | |

(Continued)

FOREIGN PATENT DOCUMENTS

WO WO 02/053212 7/2002

OTHER PUBLICATIONS

Manns et al., The acu-menTM: A new device for continuous renal replacement therapy in actue renal failure, Kidney International, 1998, pp. 268-274, vol. 54.

(Continued)

*Primary Examiner* — Manuel Mendez
(74) *Attorney, Agent, or Firm* — K&L Gates LLP (57) ABSTRACT

A renal failure therapy system includes a blood pump; a citrate pump; and a control unit configured to automatically control the blood pump and the citrate pump to achieve a citrate flowrate that is based on at least a blood flowrate.

11 Claims, 5 Drawing Sheets

(56) References Cited

U.S. PATENT DOCUMENTS

| | | | |
|---|---|---|---|
| 5,032,615 A | 7/1991 | Ward et al. | |
| 5,211,849 A * | 5/1993 | Kitaevich et al. | 604/5.04 |
| 5,252,213 A | 10/1993 | Ahmad et al. | |
| 5,378,227 A * | 1/1995 | O'Riordan et al. | 604/6.07 |
| 5,421,812 A | 6/1995 | Langley et al. | |
| 5,429,602 A | 7/1995 | Hauser | |
| 5,441,636 A | 8/1995 | Chevallet et al. | |
| 5,676,645 A * | 10/1997 | Van Waeg et al. | 604/6.07 |
| 5,709,993 A | 1/1998 | Buturovic-Ponikvar | |
| 6,042,784 A | 3/2000 | Wamsiedler et al. | |
| 6,139,748 A | 10/2000 | Ericson et al. | |
| 6,200,485 B1 | 3/2001 | Kitaevich et al. | |
| 6,217,539 B1 | 4/2001 | Goldau | |
| 6,295,990 B1 | 10/2001 | Lewis et al. | |
| 6,435,189 B1 | 8/2002 | Lewis et al. | |
| 6,471,872 B2 | 10/2002 | Kitaevich et al. | |
| 6,481,439 B1 | 11/2002 | Lewis et al. | |
| 6,548,017 B2 | 4/2003 | Krivitski et al. | |
| 6,566,402 B2 | 5/2003 | Warnock | |
| 6,575,927 B1 | 6/2003 | Weitzel et al. | |
| 6,585,675 B1 | 7/2003 | O'Mahony et al. | |
| 6,796,955 B2 | 9/2004 | O'Mahony et al. | |
| 7,004,924 B1 * | 2/2006 | Brugger et al. | 604/6.13 |
| 7,442,180 B2 | 10/2008 | Vitello et al. | |
| 8,317,750 B2 * | 11/2012 | Ware et al. | 604/131 |
| 2002/0004530 A1 | 1/2002 | Warnock | |
| 2003/0031590 A1 | 2/2003 | Park | |

OTHER PUBLICATIONS

"Continuous Hemofiltration in the Treatment of Acute Renal Failure" by L.G. Forni, M.B., Ph.D., and P.J. Hilton, M.D., St. Thomas' Hospital, London SE1 7EH, vol. 336, No. 18, pp. 1303-1309 (1997).

Morita et al., Regional Anticoagulation During Hemodialysis Using Citrate, American Journal of the Medical Sciences, Jul. 1961, pp. 72-83.

Mehta, et al., Regional citrate anticoagulation for continuous arteriovenous hemodialysis in critically ill patients, Kidney International, 1990, vol. 38, pp. 976-981.

Palsson, et al., Regional citrate anticoagulation for continuous venovenous hemofiltration in critically ill patients with a high risk of bleeding, Kidney International, 1999, vol. 55, pp. 1991-1997.

Pinnick, et al., Regional Citrate Anticoagulation for Hemodialysis in the Patient at High Risk for Bleeding, The New England Journal of Medicine, 1983, pp. 258-261.

* cited by examiner

| Fluid Source Description | Input (+) or Output (-) | Rate ml/Hr | Auto or Entered | Calculated Total Input: | Calculated Total Output: | Calculated Filtrate Pump Rate: |
|---|---|---|---|---|---|---|
| Prescribed Gain or Loss | Loss (-) | 300.0 | Entered | +950 | -200 ml/hr | 1050 ml/hr |
| Substituation Fluid | Input (+) | 490.0 | Entered | | | |
| Pump A | Input (+) | 25.0 | Auto | | | |
| Dialysate | Input (+) | 0.0 | Entered | | | |
| Pump B | Input (+) | 125.0 | Auto | | | |
| Pump C | Input (+) | 125.0 | Auto | | | |
| Pump D | Input (+) | 185.0 | Entered | | | |
| Urine Output | Output (-) | 50.0 | Entered | | | |
| Scale AA | Output (-) | 150.0 | Auto | | | |

172 — Fluid Source Description
174 — Input (+) or Output (-)
176 — Rate ml/Hr
178 — Auto or Entered
182 — Calculated Total Input
184 — Calculated Total Output
186 — Calculated Filtrate Pump Rate
188 — Check Rate Entries: Negative Filtrate Pump Rate Not Accepted
190 — Cancel Values
192 — Accept Values 86, 87, 88, 89, 90, 92, 94, 96, 98

194:
◁  Press and Hold to Increases an Input or Decrease an Output
▷  Press and Hold to Increases an Output or Decrease an Input
ENTER  Press To Enter Value Shown Above and Move to Next Pump

60

196:
Input Positive (Gain) or Negative (Loss) Amount

| 1 | 2 | 3 |
| 4 | 5 | 6 |
| 7 | 8 | 9 |
| - | 0 | + |

ENTER

FLOW BALANCING SYSTEM AND METHOD, ESPECIALLY FOR CITRATE

PRIORITY CLAIM

This application claims priority to and the benefit as a continuation application of U.S. patent application, "Flow Balancing and Synchronization System and Method Especially for Citrate," Ser. No. 12/763,864, filed Apr. 20, 2010, which is a divisional of U.S. patent application, "Medical Fluid Therapy Flow Balancing And Synchronization Method And Apparatus," Ser. No. 11/356,661, filed Feb. 16, 2006, which is a divisional application of U.S. patent application, "Medical Fluid Therapy Flow Balancing And Synchronization System," Ser. No. 10/685,724, filed Oct. 15, 2003.

CROSS-REFERENCE TO RELATED APPLICATIONS

The present Application is related to and hereby incorporates by reference the following commonly owned patent publications: "REGIONAL CITRATE ANTICOAGULATION," U.S. application Ser. No. 13/174,192; and "REGIONAL CITRATE ANTICOAGULATION," U.S. application Ser. No. 13/174,217.

BACKGROUND

The present invention relates generally to medical treatments. More specifically, the present invention relates to the synchronization of various fluids used to treat renal failure, fluid overload, congestive heart failure, drug overdoses, poisonings, immune disorders, sepsis and/or acid balance imbalances.

Due to disease, insult or other causes, a person's renal system can fail. In renal failure of any cause, there are several physiological derangements. The balance of water, minerals and the excretion of daily metabolic load are reduced or no longer possible in renal failure. During renal failure, toxic end products of nitrogen metabolism (e.g., urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life sustaining. One who has failed kidneys could not continue to live without replacing at least the filtration functions of the kidneys.

Hemodialysis ("HD"), hemofiltration, hemodiafiltration and peritoneal dialysis are types of dialysis therapies generally used to treat loss of kidney function. Peritoneal dialysis utilizes a sterile dialysis solution, or "dialysate", which is infused into a patient's peritoneal cavity and into contact with the patient's peritoneal membrane. Waste, toxins and excess water pass from the patient's bloodstream through the peritoneal membrane and into the dialysate. The transfer of waste, toxins, and excess water from the bloodstream into the dialysate occurs due to diffusion and osmosis during a dwell period as an osmotic agent in the dialysate creates an osmotic gradient across the membrane. The spent dialysate is later drained from the patient's peritoneal cavity to remove the waste, toxins and excess water from the patient.

Hemodialysis treatment removes waste, toxins and excess water directly from the patient's blood. The patient is connected to a hemodialysis machine and the patient's blood is pumped through the machine. Needles or catheters are inserted into the patient's veins and arteries to create a blood flow path to and from the hemodialysis machine. As blood passes through a dialyzer in the hemodialysis machine, the dialyzer removes the waste, toxins and excess water from the patient's blood and returns the cleansed blood back to the patient. A large amount of dialysate, for example about ninety to one hundred twenty liters, is used by most hemodialysis machines to dialyze the blood during a single hemodialysis therapy. Spent dialysate is discarded. Hemodialysis treatment lasts several hours and is generally performed in a treatment center about three times per week.

Another type of renal failure therapy is referred to generally as continuous renal replacement therapy ("CRRT"). While HD primarily relies upon diffusion to remove unwanted solutes, CRRT is a collection of subtherapies that utilize diffusion and/or convection in order to generate solute clearance, balance pH and fluid removal. During one type of CRRT, blood flows through a filter, such that a transmembrane pressure gradient between the blood compartment and the ultrafiltrate compartment causes plasma water to be filtered across the highly permeable membrane. As the water crosses the membrane, it can convect small and large molecules across the membrane and thus cleanse the blood.

CRRT has certain advantages relative to traditional dialysis therapies. A foremost advantage is the potential to effectively avoid, or at least minimize, cardiovascular instability. CRRT, in general, is a slow and continuous therapy that does not include rapid shifts in blood volume and electrolyte concentration due to the removal of metabolic products from blood as compared to intermittent forms of dialysis therapy, such as hemodialysis. Examples of continuous renal replacement therapies include continuous arteriovenous hemofiltration, continuous arteriovenous hemodialysis, continuous arteriovenous hemodiafiltration, continuous venovenous hemofiltration, continuous venovenous hemodiafiltration, continuous venovenous hemodialysis, slow continuous ultrafiltration, hemoperfusion and continuous ultrafiltration with periodic intermittent hemodialysis.

Hemofiltration, one type of CRRT, is an effective convection-based blood cleansing technique. Blood access can be venovenous or arteriovenous. As blood flows through the hemofilter, a transmembrane pressure gradient between the blood compartment and the ultrafiltrate compartment causes plasma water to be filtered across the highly permeable membrane. As the water crosses the membrane, it convects small and large molecules across the membrane and thus cleanses the blood. A large amount of plasma water is eliminated by filtration. Therefore, in order to keep the body water balanced, fluid must be substituted continuously by a balanced electrolyte solution (replacement or substitution fluid) infused intravenously. This substitution fluid can be infused either into the arterial blood line leading to the hemofilter (predilution), into the venous blood line leaving the hemofilter (postdilution) or both. Another type of therapy, hemodiafiltration, combines the diffusion and convective cleansing modes of hemodialysis and hemofiltration. The present invention expressly applies to each of the therapies mentioned herein including, additionally TPE, cytopheresis and hemoperfusion.

Each of the renal failure therapies involves the flow and control of multiple fluids. Some commercially available replacement or substitution fluids, for example, are lactate-based solutions. In certain instances, such as with patients with multiple organ failure, the use of the physiological buffer bicarbonate is preferred over lactate. It is common practice to manually prepare solutions buffered with bicarbonate extemporaneously. This is typically carried out by adding the prepared bicarbonate solution to an existing injectable quality solution to form the bicarbonate-based solution prior to administration to the patient. For example, it is known to add bicarbonate to an acidic electrolyte concentrate solution, which is in direct contact with administration tubing connected to the patient prior to administration thereof to the patient. It is also common practice to manually inject other electrolytes, such as potassium chloride, directly and separately into the bicarbonate-based solution prior to administration. The physical handling of the fluids can become tedious and time-consuming.

It should be appreciated that for each of the above-described types of renal failure therapies, transferring and monitoring the flowrate and the total volume of fluid delivered for multiple types of fluids as well as adhering to certain therapy restrictions (e.g., a first fluid must be flowing to or from the patient to enable a second fluid to flow) each create a control dilemma. Managing a patient's total fluid balance often involves obtaining the patient's prescribed net fluid loss or gain and manually summing various fluid inputs and fluid outputs to arrive at a necessary removal rate, which is then entered into a renal failure therapy machine, such as a dialysis machine or a CRRT machine. For example, if a patient is prescribed to have a net fluid loss (ultrafiltrate removal above and beyond patient fluid input but taking into account other sources of fluid output) of two hundred milliliters ("ml") per hour ("hr"), is receiving one hundred ml/hr of fluid via an intravenous ("IV") pump and has fifty ml/hr of urine output, the operator would have to calculate and instruct the renal failure therapy machine to remove two hundred fifty ml/hr of ultrafiltrate above and beyond replacement of substitution fluid that is being delivered by the CRRT or dialysis machine, so that the net total volume of fluid (removed) over the hour is two hundred ml.

The above example used only one IV fluid. It is possible however to have multiple IV or administration fluid inputs, making the above-described process even more involved and error prone. A need therefore exists to provide an improved system for calculating, balancing, synchronizing and controlling the delivery of multiple fluids in a renal failure therapy.

SUMMARY

The present invention provides a system, apparatus and method that allow external infusion, IV or administration pumps to be synchronized with the internal pumps of a medical fluid therapy machine. The system reduces the time and effort needed to calculate, set-up, enter and maintain flowrates of various fluids, maintained internally or externally with respect to the medical fluid therapy machine. The system also automatically follows therapy requirements, for example, a requirement that one pump/fluid be running/flowing for another pump/fluid to be enabled to run/flow. The system further automatically adjusts for variations in flowrate of one fluid with respect to another. For example, filtrate/output pump internal to the machine may increase or decrease in response to the flowrate or output rate of a manually entered value of an external pump or measuring device. In short, the system provides a more "hands-off", safe and effective method and apparatus for medical fluid therapy delivery and removal.

"Medical fluid therapy" as used herein includes, but is not limited to peritoneal dialysis, hemodialysis, hemofiltration, hemodiafiltration, therapeutic plasma exchange, cytopheresis, hemoperfusion and continuous renal replacement therapy (wherein CRRT includes continuous arteriovenous hemofiltration, continuous arteriovenous hemodiafiltration, continuous arteriovenous hemodialysis, continuous venovenous hemofiltration, continuous venovenous hemodialysis, continuous venovenous hemodiafiltration, slow continuous ultrafiltration, and continuous ultrafiltration with periodic intermittent hemodialysis) and any combination thereof. The invention includes a communication system in which a medical fluid therapy machine sets, monitors, retrieves information from and controls pump flowrates for pumps both integral and external to the machine. The system thereby achieves a desired positive, neutral or negative net volume of fluid flow to or from a patient over a given period of time.

The system enables an operator to enter, retrieve and/or store initial settings for the pumps (integral and/or external), wherein one or more of the pumps can be dependent upon the operation of one or more other pumps. For example, the operator could set a particular external infusion pump to synchronize with the internal blood pump. In such a case, the medical fluid therapy machine would, for example, command the infusion pump to run when the blood pump is running and to pause when the blood pump stops running.

The system also enables the operator to enter a desired net loss or gain amount, wherein the system automatically calculates and adjusts the various internal and external input and/or output flowrates associated with the therapy to achieve the entered net loss or gain of fluid. The system facilitates communication between pumps and sensors located inside the medical fluid therapy machine with pumps and measuring devices located external to such machine.

The system reduces substantially the amount of manual flowrate calculations that have heretofore been required. Further, instead of requiring the operator to manually set and inject or infuse one or more administration fluids, the system automatically sets and controls such injection/infusion. Moreover, during therapy the system can sense the actual amount of fluids flowed and compare same to the required amount and adjust the flowrates of the fluids accordingly and "on the fly" or substantially "on the fly."

The system includes a number of modes of communication for allowing the external input/output devices to share information with the medical fluid therapy machine, including wired (e.g., fiber optic cable) or wireless modes (e.g., RF signal) of communication. The machine communicates with the external input/output devices to communicate or retrieve information or send commands, such as: device on, device off, start pump, stop pump, pump rate, volume to be infused, clear rate infused/removed, name of drug/solution being infused/removed and concentration of drug/solution being infused/removed, etc.

The fluids balanced and controlled by the system of the present invention vary depending upon the patient's needs and upon on the medical therapy used. In the case of diffusive therapies, a dialysate will be used to absorb toxins and other waste materials. In the case of convective therapies, an infusate or replacement fluid will be used. Each type of therapy is associated with its own set of IV or administration fluids. A patient undergoing renal therapy may also be receiving medication or infusions, such as heparin, calcium, magnesium, total parenteral nutrition ("TPN") or vasoactive drugs such as dobutamine, dopamine, nitroglycerin, etc. While those medications are typically stored and pumped by an outside pumping device, an internal pumping device may alternatively pump such medications.

An anticoagulant, such as heparin or citrate, could additionally be stored and pumped from an external or internal pump or storage device. The ability to synchronize anticoagulants, and in particular citrate, to the blood pump, is critical. Setting the input of citrate to be synchronized with or to follow variations in blood flowrate and having the ability to balance the flow of citrate to a prescribed setting is particularly advantageous.

The system uses the controller of the machine to control all fluids, internal or external, via a communication link to a remote controller associated with each of the external pumps. The system also retrieves volumes delivered or rates of administration by external devices and addresses those fluids with respect to the internal fluid balancing monitored and controlled by the system to achieve the overall desired patient fluid balance.

It is therefore an advantage of the present invention to provide an improved medical fluid therapy control system, apparatus and method.

It is another advantage of the present invention to streamline the fluid flow control for a medical fluid therapy, such as peritoneal dialysis, hemodialysis, continuous arteriovenous hemofiltration, continuous arteriovenous hemodialysis, continuous arteriovenous hemodiafiltration, continuous venovenous hemofiltration, continuous venovenous hemodialysis, continuous venovenous hemodiafiltration, slow continuous ultrafiltration, hemoperfusion, continuous ultrafiltration with periodic intermittent hemodialysis, therapeutic plasma exchange, cytopherisis and any combination thereof.

It is a further advantage of the present invention to simplify the start-up of a medical fluid therapy.

It is yet another advantage of the present invention to simplify the fluid flow maintenance of a medical fluid therapy.

It is yet a further advantage of the present invention to improve the flow delivery accuracy of a medical fluid therapy.

It is still another advantage of the present invention to reduce the possibility for error in a medical fluid therapy.

Moreover, it is an advantage of the present invention to increase the flexibility of a medical fluid therapy with respect to adjusting flowrates on the fly and over multiple therapy sessions or to adjust the flowrates of one or more pump(s) in response to the rate of input or output of one or more fluid delivery or output measuring device(s).

Yet another advantage of the present invention is to balance and synchronize the flowrate of an anticoagulant such as citrate.

Additional features and advantages of the present invention are described in, and will be apparent from, the following Detailed Description of the Invention and the figures.

DETAILED DESCRIPTION

The present invention is useful for medical fluid therapies, including but not limited to peritoneal dialysis, hemodialysis and CRRT (wherein CRRT includes continuous arteriovenous hemofiltration, continuous arteriovenous hemodialysis, continuous arteriovenous hemodiafiltration, continuous venovenous hemofiltration, continuous venovenous hemodialysis, continuous venovenous hemodiafiltration, slow continuous ultrafiltration, hemoperfusion, therapeutic plasma exchange, cytopheresis, continuous ultrafiltration with periodic intermittent hemodialysis), fluid overloads, congestive heart failure, drug overdoses, poisonings, immune disorders, sepsis, acid imbalances and any combination thereof. The invention includes a network that, for any of the above therapies, enables pumps external to a main therapy machine to be synchronized and controlled automatically with pumps provided integrally with the machine. The system reduces the setup time associated with competing systems, automatically follows therapy requirements, automatically adjusts for variations in flowrate of one fluid with respect to another and in general provides a safe and effective method and apparatus for controlling a renal failure therapy.

Figure 1:
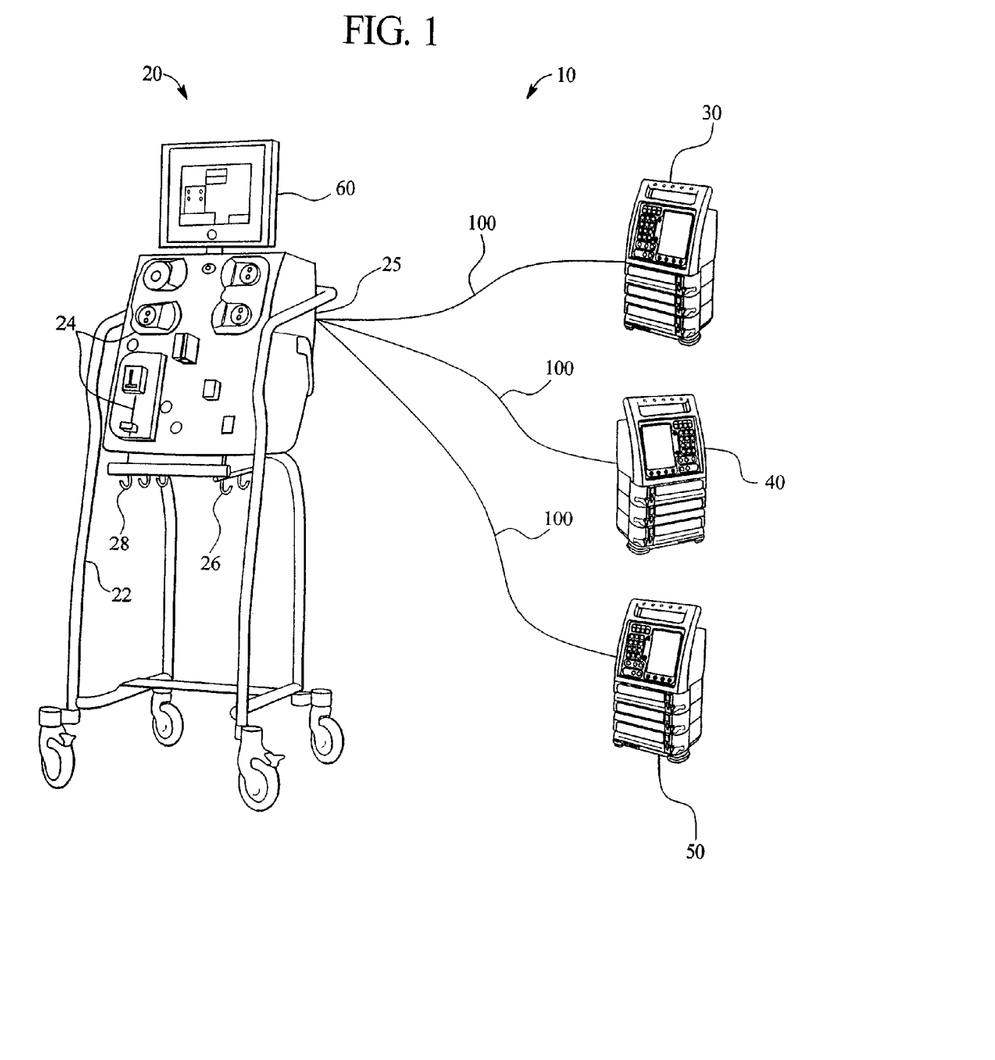
FIG. 1 is a perspective view of a medical fluid therapy machine and various input/output devices located externally from the machine.

Referring now to the figures and in particular to FIG. 1, a synchronization system or network 10 is illustrated. The system or network 10 encompasses a medical fluid therapy ("MFT") machine 20 and one or more external input/output devices 30, 40 and 50. MFT machine 20 can for example be a hemofiltration machine, however, machine 20 alternatively performs any of the medical fluid therapies described above or combinations thereof.

MFT machine 20 includes a controller, which is described in more detail below. That controller communicates with external input/output devices 30, 40 and 50 via communication links 100. Communication links 100, in one embodiment, are hard-wired or a cabled connections, such as electrical cables, data lines, analog or digital signals, local or wide area links, Internet links, or fiber optic links. In another embodiment, the communication links are wireless, such as a remote frequency ("RF") links, ultrasonic links, photoelectric links, microwave links or the like. Combinations of the above different methods of communication are also contemplated.

As shown in more detail below, MFT machine 20 includes a multitude of onboard or integral pumps, which each pump a different fluid. External devices 30, 40 and 50 may be any type of device common to medical fluid therapies, some of which are described in more detail below. Each of those devices includes, in one embodiment, a separate pump, which is connected to either a source of fluid or a drainage container or outlet. Each of the devices 30, 40 and 50 also includes a microprocessor or other type of controller that is able to: (i) receive a command from MFT machine 20 and send a status signal back to the MFT machine 20.

MFT machine 20 and the external input/output devices 30, 40 and 50 each, in one embodiment, include an address that distinguishes MFT machine 20 from other such machines and external input/output devices 30, 40 and 50 from other like devices. The addresses designate the pumps of the MFT machine 20 and of the external input/output devices 30, 40 and 50 to be associated with a specific patient that is undergoing hemofiltration therapy. The addresses prevent miscommunication between multiple MFT machines 20 and associated input/output devices 30, 40 and 50 if multiple therapies are taking place simultaneously, for example, in a treatment center. The potential for miscommunication exists especially with wireless communication between the machine 20 and the external input/output devices. Such potential for miscommunication could also occur if, for example, the network enables one of a plurality of computers located remotely from the MFT machine 20 to be used to synchronize with multiple internal and external pumps of the therapy. Further, it is possible that one or more remote administration pumps is fluidly coupled to multiple MFT machines 20 or to multiple patients. In such a case, the controller for the administration pump needs to know the address of the MFT machine 20 needing fluid to be added or removed.

As illustrated, MFT machine 20 includes a housing 25 that houses the major components of the machine, such as a blood pump, dialysate or replacement fluid pump, a hemofilter/dialyzer, other onboard pumps and other components, such as, pressure sensors, air detectors, flow meters and the like. MFT machine 20 also includes a graphical user interface ("GUI") 60, which enables the operator to run the MFT machine GUI 60 is discussed in more detail below in connection with FIGS. 4 and 5.

In general, the GUI 60 operates with one or more microprocessors, which can be housed either inside GUI 60 or housing 25. Although GUI 60 is shown connected to housing 25, it is also possible that GUI 60 is located on an external PC, which is connected to housing 25 via a computer cable, such as a serial or parallel data transmission cable. The remote GUI 60 enables system 10 in one embodiment to be commanded through a central computer, which communicates and operates with a plurality of different MFT machine housings 25. In still a further alternative embodiment, the flow components within housing 25 as well as the pumps of external input/output devices 30, 40 and 50 communicate with GUI 60 over a local area network ("LAN") or wide area network ("WAN"), such as the Internet. It is therefore possible for an operator to control (send and receive commands/feedback) via a remote GUI 60 the operation of the MFT machine 20 and the external input/output devices 30, 40 and 50 for a patient who is at home.

As illustrated by rolling frame 22, MFT device 20 can be moved or oriented to a position that is convenient for operation. Additionally, MFT machine 20 includes various exterior apparatus 24, which are common to MFT machines generally. Further, MFT machine 20 includes scales 26 and 28 that enable the weight and thus the volume of one or more fluids, such as dialysate, replacement fluids or collected urine, to be determined. For instance, scale 26 is used in one implementation to monitor the substitution fluid/dialysate flow, while scale 28 is used to monitor the flow of ultrafiltrate.

Figure 2:
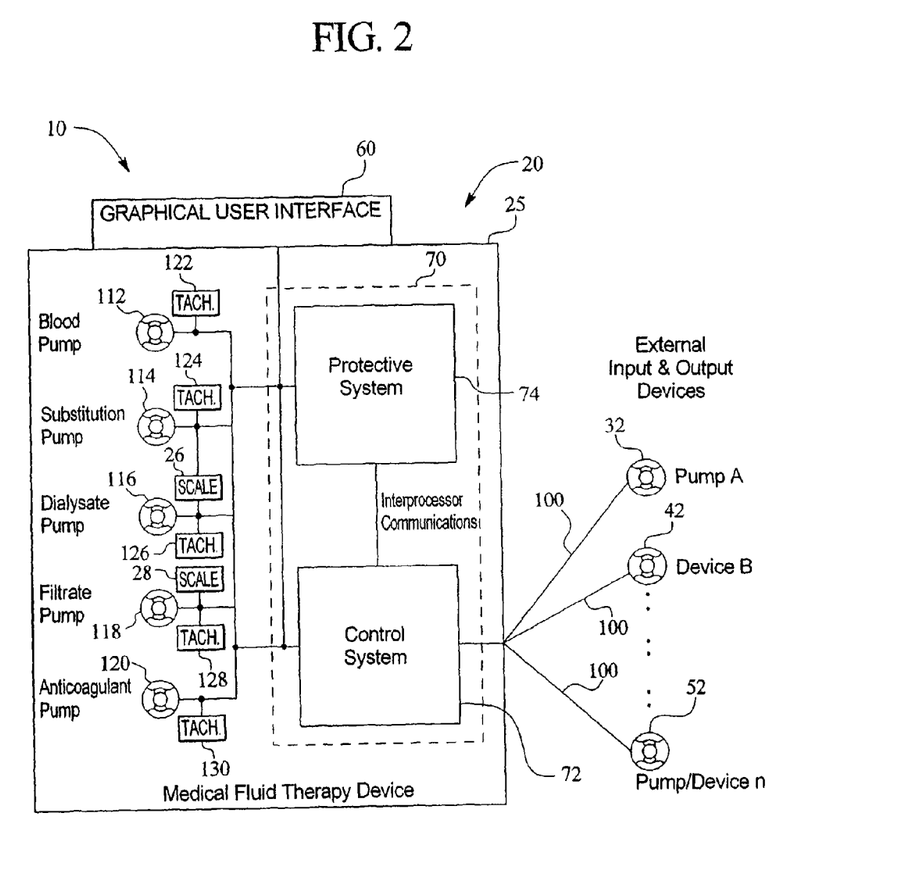
FIG. 2 is a schematic illustration of one embodiment of the pump synchronization system of the present invention, which shows a simplified electrical configuration thereof.

Referring now to FIG. 2, a schematic electrical diagram is shown for the machine 20 of the pump synchronization system 10 of the present invention. The schematic includes the housing 25 of MFT machine 20 discussed above in connection with FIG. 1. MFT machine 20 includes in housing 25 a plurality of different pumps. In the illustrated embodiment, the MFT machine 20 houses a blood pump 112, a substitution pump 114, a dialysate pump 116, a filtrate pump 118 and an anticoagulant pump 120 (e.g., for hemodiafiltration that uses both diffusive and connective clearance modes). Each of the above-described pumps is common to an MFT machine. Blood pump 112 pumps blood from a patient through a filter, such as a dialyzer or hemofilter, and back to the patient. The substitution pump 114 pumps replacement fluid directly into the patient's blood flow line either prior to or after a dialyzer or hemofilter. As stated above, hemofiltration is a convective process that adds injectable quality fluid directly to the patient's blood, while a hemofilter removes ultrafiltrate from the patient's blood. In essence, hemofiltration exchanges the waste from the patient's blood directly with an injectable quality solution such as a sterile solution.

FIG. 2 also illustrates a dialysate pump 116. Dialysate pump 116 is provided typically in hemodialysis, but can also be used as illustrated in combination with hemofiltration (e.g., for hemodiafiltration). Dialysate pump 116 pumps dialysate into one end of a dialyzer. That dialysate absorbs waste flowing across membrane walls within the dialyzer, such as, sodium, potassium, phosphate, creatinin. Dialysate pump 116 therefore performs a similar function as the substitution pump 114 in that both pumps pump an injectable quality biologically compatible fluid into either direct contact or transmembrane contact with at least the waste components of patient's blood.

In either situation, whether a dialyzer or a hemofilter is used, a filtrate pump 118 is employed to remove ultrafiltrate from the patient's blood. That is, whether a hemofilter or a dialyzer is employed, the filtrate pump 118 is used to pull fluid from one of those devices to remove waste products and excess liquid from the patient's blood.

Anticoagulant or syringe pump 120 operates in a similar manner to substitution pump 114 to supply an anticoagulant to the patient's blood flow line directly. Anticoagulant pump 120 is alternatively located external to machine 20 and communicates with controller 70 via a link 100. For purposes of the present invention it does not matter which pumps are located internal or external to machine 20 as long as a mode of communication exists via either internal wiring or an external link 100.

In the illustrated embodiment, tachometers or flowmeters 122 to 130 are provided and operate with pumps 112 to 120, respectively. Tachometers 122 to 130 are of any type known to those of skill in the art to monitor the pumps, which are accurate and non-invasive. Tachometers 122 to 130 are placed adjacent to or in relatively direct fluid communication with lines leading directly to or from pumps 112 to 120. Feedback from tachometers 122 to 130 for pumps 112 to 120, respectively, is sent electronically to a controller 70. The pumps 112 to 120 are also each connected to or in communication with the controller 70, which in the illustrated embodiment is also housed within housing 25. Controller 70 is also operably connected to the GUI 60.

FIG. 2 illustrates that the filtrate pump 118 also operates with a scale, such as scale 28, which produces a weight or mass signal that is sent electronically to controller 70. Furthermore, substitution pump 114 and dialysate pump 116 also operate with a shared scale, such as scale 26, which produces a weight or mass signal that is sent electronically to controller 70. Other scale arrangements are possible. FIG. 2 illustrates that an electrical or signal type communication further exists between each of the external pumps 32, 42 and 52 and controller 70.

As illustrated, controller 70 is a multiprocessor type controller in one embodiment. That is, controller 70 includes a first processor 72, or control processor, which communicates with the pumps (pump controllers) to send and receive information to and from the pumps. Processor 72 also communicates with other devices located within MFT machine 20, such as the pressure sensors, temperature sensors, concentration sensors, air detectors, blood detectors and the like. Control processor 72 operates further with each of the other electrical components of machine 20, such as lights, audio outputs, switches, etc.

Control processor 72 communicates with a second or safety processor 74, which in turn communicates with each of the pumps 112 to 120. Safety processor or protective processor 74 monitors the pumps 112 to 120 for error conditions, such as, communication loss, framing errors, invalid packet format, data errors and the like. Safety processor 74 receives status and parameter information from pumps 112 to 120 to ensure that the pumps and each of the fluids pumped thereby are operating within predefined safety limits. Safety processor 74 in turn handshakes with control processor 72.

While controller 70 is shown having two processors 72 and 74 working in cooperation, it is possible that controller 70 includes additional processors. For example, controller 70 in an alternative embodiment includes an additional supervisory processor that runs delegate processors, such as processors 72 and 74. A separate processor is also provided in one embodiment to operate GUI 60. That processor can, for example, run software that enables the machine 20 to be controlled over a network, such as the Internet. In the illustrated embodiment, GUI 60 communicates with both processors 72 and 74 of controller 70. It is also possible that controller 70 includes a single processor operating both independent control and safety tasks.

Control processor 72 also communicates via links 100 (including each of the alternatives for links 100 described above) with a plurality of external input/output pumps/controllers 32, 42 and 52. Pumps/controllers 32, 42 and 52 are provided, for example, within external input/output devices 30, 40 and 50, shown above in connection with FIG. 1.

Control processor 72, located within housing 25 of machine 20 as illustrated, controls pumps and pump controllers 112 to 120 that are housed within machine 20 as well as pumps/controllers 32, 42 and 52 located external to machine 20. Processor 72 sends instructions to the internal and external pumps, such as device on, device off, start pump, stop pump, pump rate, volume to be infused, clear rate infused, name and concentration of drug/solution being infused. The pumps or the controllers operating the pumps in turn send messages back to processor 72 via the hardwired links 100 or the wired or wireless links 100 existing between processor 72 and external pump controllers 32, 42 and 52. The status messages returning from the pumps controllers include typically: channel identifier, channel status, rate, dose, volume remaining, infusion label, flow check, primary volume infused, piggyback volume infused and volume history last cleared. Each of those messages is known to those of skill in the art. For example, the "channel status" is a monitoring of the pump's exception status, which includes information such as: no exception, battery low alert, lithium battery low alert, channel stopped alert, changing piggyback program alert, programming piggyback alert, keep vein open ("KVO") alert, piggyback call back alert, priming alert, dose out of range alert, battery depleted alarm, tube not loaded alarm, tube misloaded alarm, tube loading alarm, close regulating clamp alarm, incomplete piggyback program alarm, incomplete primary program alarm, piggyback out of range alarm, primary out of range alarm, air in line alarm, downstream occlusion alarm, upstream occlusion alarm, reset manual tube release alarm, temperature too high alarm, temperature too low alarm and channel failure.

As illustrated above, there exists a wealth of information that is communicated between control processor 72 of machine 20, the internally located pumps 112 to 120 and the externally located pumps 32, 42 and 52. As illustrated below, maintaining control of pumps located both inside and outside of machine 20 provides many advantages with respect to the overall operation of the therapy. It should be appreciated that while in one preferred embodiment controller 70 and processors 72 and 74 are located within housing 25 of machine 20, it is also possible that such control be maintained on an external PC, on a local area network or on a wide area network such as the Internet.

Figure 3:
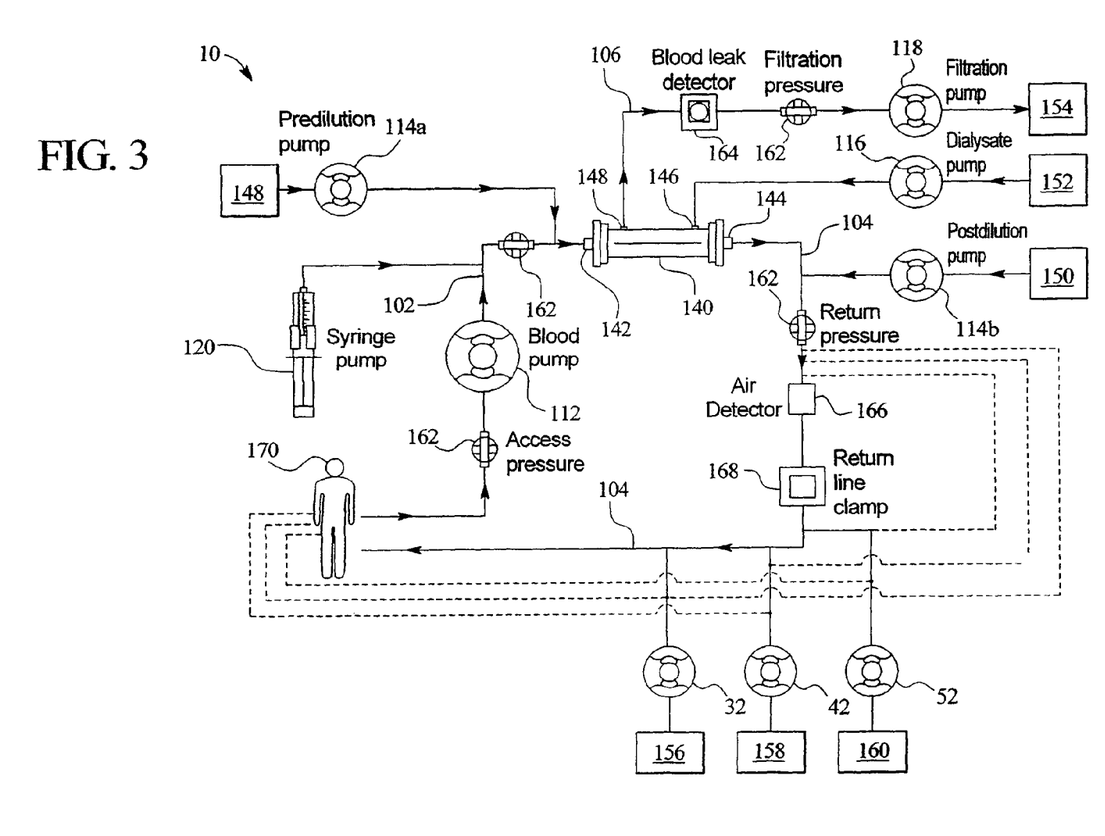
FIG. 3 illustrates one embodiment of a flow schematic of the present invention showing the operation of various pumps located internally and externally with respect to a medical fluid therapy machine.

Referring now to FIG. 3, one possible flow schematic for the system 10 is illustrated. The flow schematic shows a hybrid of the hemofiltration and hemodialysis therapies (sometimes called hemodiafiltration). In the illustrated embodiment, system 10 operates with a hemodialyzer or hemofilter 140. Hemodialyzer or hemofilter 140 includes a blood inlet 142 and a blood outlet 144. Hemodialyzer 140 also includes a dialysate inlet 146 and an ultrafiltrate outlet 148. The primary difference between a hemodialyzer, such as dialyzer 140, and a hemofilter is that the hemofilter typically has a greater porosity to allow for the movement of large quantities of plasma water across the membrane. Hemofiltration relies upon makeup fluid being added via the substitution pumps 114a and 114b.

As illustrated, system 10 in FIG. 3 includes two substitution pumps 114a and 114b. Substitution pump 114a is a predilution pump, which injects substitution fluid into blood line 102 prior to the blood inlet 142 of dialyzer 140. Substitution pump 114b, on the other hand, is a postdilution pump which injects the same or different substitution fluid into blood line 104 after the blood exit 144 of dialyzer 140. As illustrated, predilution substitution pump 114a pulls fluid from source 148, while postdilution substitution pump 114b pulls fluid from source 150. The predilution and postdilution fluids can be the same or different. The dialyzer 140 receives dialysate via pump 116 from one or more dialysate supply 152. In a similar manner, filtration pump 118 pulls ultrafiltrate through exit port 148 of dialyzer 140 to one or more an ultrafiltrate bag 154.

In FIG. 3, the anticoagulant pump 120 is a syringe-type pump which is known in the art. The anticoagulant is pumped in a similar manner to a predilution substitution fluid into blood line 102 located upstream of dialyzer 140. The anticoagulant can be of any suitable type, such as heparin or citrate.

External pumps 32, 42 and 52 are fluidly connected to the patient's bloodline 104. In FIG. 3, pumps 32, 42 and 52 feed fluid to blood return line 104. Alternatively, one or more or all of the remote administration pumps 32, 42 or 52 fluidly communicates with the blood line 102, e.g., prior to dialyzer 140, or with the return line 104 upstream of the air detector 166, as shown by phantom lines leading to such upstream point. Alternatively, one or more or all of the remote administration pumps 32, 42 or 52 fluid communicates directly with the patient 170 as shown by phantom lines leading to patient 170 and does not connect to bloodline 102 or bloodline 104. In FIG. 3, each of the pumps controllers 32, 42 and 52 is shown pulling fluid from supplies 156, 158 and 160, respectively, to return line 104. Supplies 156, 158 and 160 can include any suitable or desirable fluid, such as heparin, citrate or other anticoagulant, crystalloid, colloid, concentrate, an administration fluid, an electrolyte solution, an intravenous fluid, an antibiotic, a vasoactive drug, a total parenteral nutrition solution, an enteral nutrition solution fluid, fluid via feeding by mouth, fluid via feeding by tube and any combination thereof.

As discussed above, system 10 includes a number of sensors controlled by control processor 72. For instance, control processor 72 monitors inputs from various pressure sensors 162. Further, a blood leak detector 164 is placed in the ultrafiltrate line 106 to look for any blood cells, platelets or other desirable blood components that have improperly passed through the walls of the membranes contained within dialyzer 140. Processor 72 also receives signals from air detector 166, which detects air in the blood line that may return to the patient 170. If air is detected, controller 70 immediately sends a signal to the blood pump 112 and clamp 168 to stop the flow of blood to and from the patient 170.

In operation, blood pump 112 pulls blood through blood removal line 102, pumps the blood through dialyzer 140 and returns the blood to the patient 170 via return line 104. In the process, the blood receives an anticoagulant and a predilution substitution fluid in blood withdrawal line 102. The blood is then dialyzed or cleaned by diffusion via dialysate, which is pumped outside of the membranes carrying the blood within the dialyzer 140. The blood then receives more substitution fluid on the postdilution line. The remote administrate pumps 32, 42 and 52 also inject certain additives into blood return line 104, blood removal line 102 and/or directly to patient.

Figure 4:
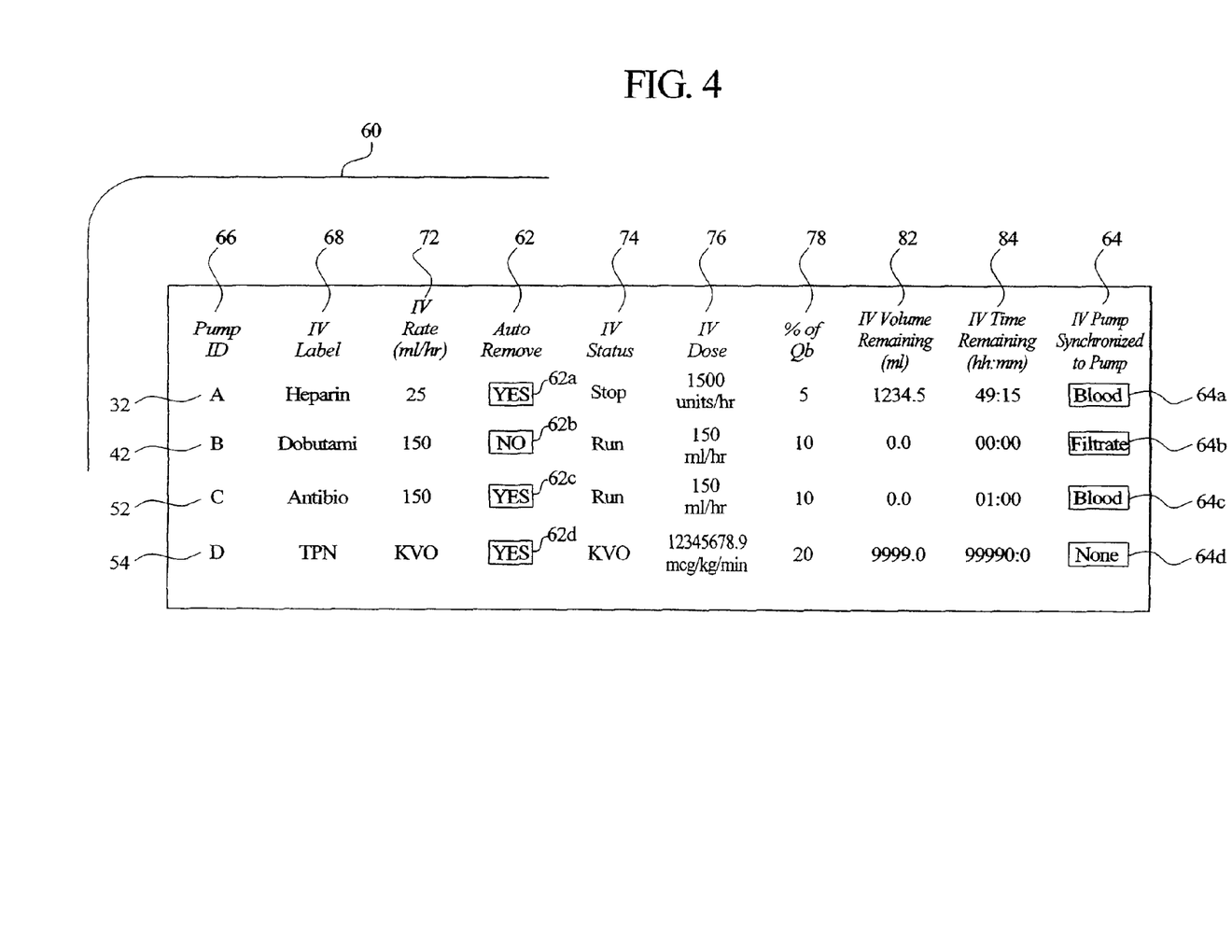
FIG. 4 is an input screen of a graphical user interface ("GUI") operating with the medical fluid therapy machine showing the interrelation between and control of various pumps controlled by the synchronization network of the present invention.
Figure 5:
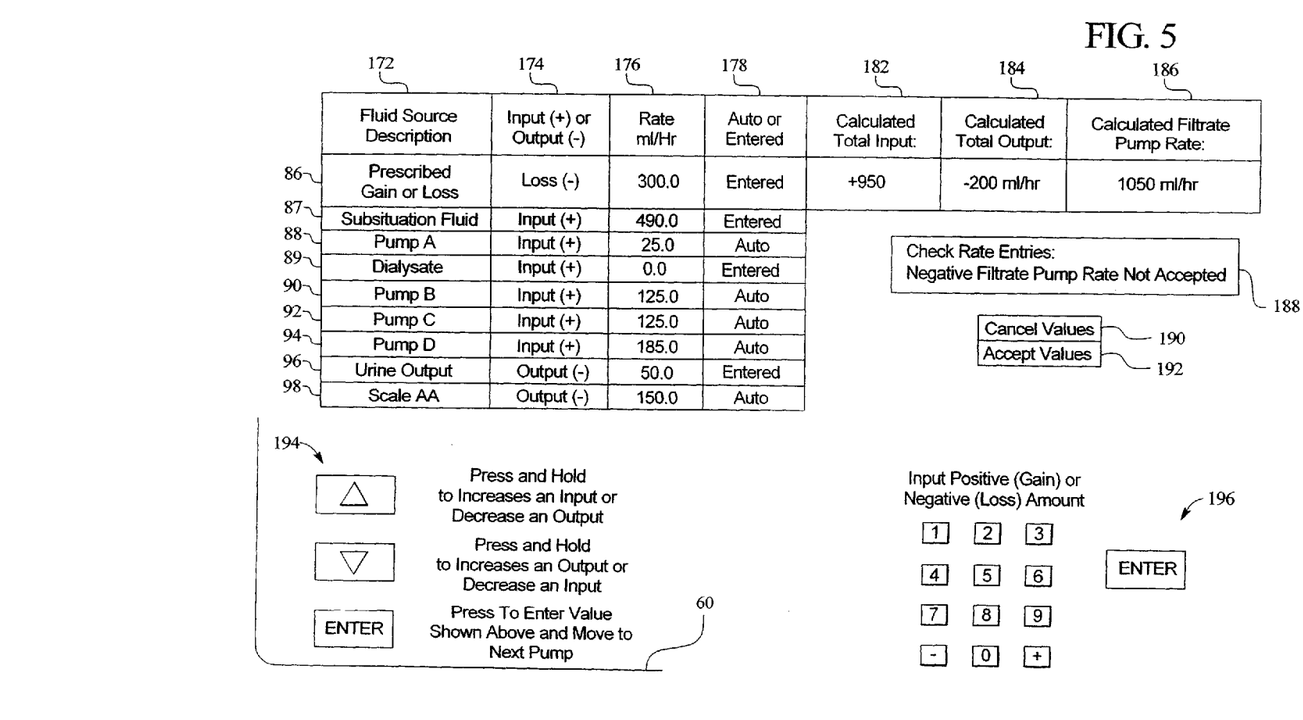
FIG. 5 is an additional input screen of the GUI illustrating a flow calculation that is made automatically by the system of the present invention.

Referring now to FIGS. 4 and 5, various screen shots of GUI 60 illustrate the synchronization and calculation features of the pumping system 10 of the present invention. In particular, FIG. 4 illustrates the synchronization of the pumps, while FIG. 5 illustrates the calculation feature of system 10. It should be appreciated that not all of the information disclosed in FIGS. 4 and 5 has to be displayed on GUI 60. Further, additional information may be displayed on different screens in combination with the information shown in FIGS. 4 and 5 or in separate screens on GUI 60. Still further, the system is not required to operate with a touch screen and can alternatively or additionally operate with electromechanical input devices, such as knobs, push buttons, switches and the like.

GUI 60 of FIG. 4 illustrates that system 10 provides the MFT machine 20 the ability to start and stop various pumps automatically or manually based on operator selectable settings for the auto-remove column 62 shown on GUI 60. As illustrated, pumps 32, 52 and 54 are each selected for auto removal. That is, those pumps are set to automatically start and stop without any additional input from the operator. In one preferred embodiment, GUI 60 provides an operator override to manually shut off a pump that is currently being controlled automatically. For example, areas 62a to 62d on GUI 60 in an embodiment are associated with a touch screen interface, wherein an operator can touch, for example, input 62a to change the state from auto-remove to no-auto-remove. The no-auto-remove state can be set to default to a pump-off condition, so that changing from auto-remove to manual operation effectively reduces an input or output total flowrate by the pump rate of the associated pump. The operator can thereafter start/stop the pump via a separate input.

As illustrated, Pump B (element number 42) is currently running as indicated by column 58. The pump 42 is not set to auto-remove, so that the pump requires an external start input to initiate flow. Pump B, however, is synchronized with the filtrate pump to only run when the filtrate pump is running, as indicated by column 64.

Column 64 indicates the pump, if any, to which the automatically controlled pumps are synchronized. As illustrated, IV pumps 32 and 52 are synchronized to pump when the blood pump is pumping and not pump when the blood pump is not running. IV pump 42 is set to be synchronized with the filtrate pump, e.g., to pump when the filtrate pump is pumping and not pump when the filtrate pump is not pumping. IV pump 54, while being controlled automatically, is not tied to the flow or pumping of any other pump. In such a case, control processor 72 can intermittently send a signal to start and stop IV pump 54. Inputs 64a to 64d enable an operator to change the pumps to which the IV pumps are synchronized. Inputs 64a to 64d can be toggled inputs, be selected from a displayed group, or enable the operator to key in the pump name from a keyboard. In an alternative embodiment, such synchronization is predetermined by a physician and set to be locked so that the setting is not changeable.

Column 66 provides a pump identifier. Column 68 specifies the drug or other fluid that is to be injected via the external IV or administration pump. Column 56 sets forth the desired flowrate for the drug, e.g., by setting a flowrate amount (ml/hr) or by setting a condition, such as a keep vein open condition. Column 58 illustrates the current status of the particular pump. For example, pumps 42 and 52 are currently running, while pump 32 is stopped. Column 76 illustrates the IV dose for each of the drugs or fluids, which is a calculated value (performed automatically by some external pumps) and is typically the drug's concentration per time unit and/or per patient weight. Column 78 represents the percent of total flowrate of the particular drug being pumped by pumps 32, 42, 52 and 54. Column 82 sets forth the amount of fluid remaining in the supplies for pumps 32, 42, 52 and 54, respectively. Column 84 sets forth the amount of time remaining to complete the infusion of a particular drug via one of the pumps 32, 42, 52 and 54.

FIG. 4 illustrates that one of the remote IV or administration pumps can be tied to one of the integrally located pumps, such as the blood pump. Other remote pumps could be tied to or dependent upon the integral filtrate pump, or to another remote pump. In a similar manner, one of the internally housed pumps can be tied to or dependent upon the flow of another one of the internally housed pumps or to the flow of a remote pump. For example, the dialysate flow could be tied to or dependent upon the pumping of blood or vice versa.

Importantly, system 10 of MFT machine 20 commands certain remote pumps set to be under automatic control, enabling the operator to perform other tasks. Such remote control is also performed without the possibility of being effected by human error. Safety processor 74 double checks to ensure that a particular IV pump is on when it is supposed to be on and vice versa. Because the control is centralized within the MFT machine 20, safety processor 74 can make such a determination based on the knowledge of the flow scheme set in or programmed into software and the feedback being provided by remote devices 30, 40 and 50.

System 10 increases accuracy and safety and reduces the amount of human input and attention that is needed with known systems, wherein known systems require the external infusion pumps to be operated independently from the main therapy machine. In known therapy systems, if the main therapy machine is used to manage the patient's total fluid balance, the fluid balancing must be done manually by an operator adding various patient inputs, outputs and calculating an actual removal rate that is needed to achieve a desired removal rate. The system 10 performs such total fluid balancing automatically. Indeed, system 10 enables the operator to simply enter the desired fluid loss or gain, wherein the system controls either the filtrate output, the substitution fluid inlet or both to achieve the inputted loss/gain.

Additionally, system 10 looks at the input and output pumps, including the substitution pumps 114, the filtrate pump 118 and the anticoagulant pump 120 to determine the actual filtrate or substitution fluid rate needed. That is, the system 10 looks at the substitution pump and anticoagulant syringe pump to see if the actual flowrate is the same, less than or more than the entered or expected flowrate. If so, system 10 automatically adjusts the filtrate or additive rate to achieve the desired loss/gain amount.

FIG. 5 illustrates the calculation feature of the present invention. In FIG. 5, the internal flowrates, such as the substitution fluid or the dialysate input are shown by rows 87 and 89. The infusion or administration pumps A to D are represented by rows 88 to 94. The output pumps are indicated by rows 96 and 98. The calculation feature provides a tool that simplifies operation and reduces errors in connection with setting the prescribed patient gain or loss rate. The operator sets the IV pumps to either be automatically controlled or manually controlled, for example, via buttons 62a to 62d in FIG. 4. Any of the automatically controlled pumps is thereafter controlled via system 10 without operator input, except in emergency situations. In FIG. 5, the operator enters the patient's urine output as seen in row 96, the substitution fluid rate, as indicated by row 87, the dialysate input as indicated by row 89 and the desired patient net gain or loss as indicated by row 86. The urine output in row 96 is alternatively measured and inputted via a measuring device, such as via scales 26 and 28 in FIG. 1.

Column 172 describes the fluid source/pump, or in the case of row 86, the net desired gain or loss. Column 174 indicates whether the associated external device will infuse a component into the patient or monitor the removal of a component from the patient. Column 176 indicates the flowrate for the source or output shown in column 172. Column 178 shows whether the flowrate information is automatic, e.g., set in software, or otherwise permanently set or entered, e.g., by the operator or via measurement and feedback from a device, such as feedback from a urine measurement device. Further, the automatically entered flowrates could be based on a predefined percentage of the net fluid loss rate or be prescribed by a physician.

Entry 182 shows the total flowrate of all the inputs from rows 87 to 94. The equation used to determine the calculated filtrate actual pump rate shown in entry 186 is:

Filtrate pump rate=total input rate−total external output rate+prescribed net loss rate.

By that equation, the total input rate of nine hundred fifty ml/hr, which is the sum of all the infusion pumps (rows 88 to 94) plus the substitution fluid pump (row 87), is shown in entry 182. System 10 automatically subtracts the calculated total output rate of two hundred ml/hr shown in entry 184, which is the sum of the patient's urine output in column 96 plus a Scale AA output shown in column 98. The total input rate less the total external output rate is seven hundred fifty ml/hr. Scale AA it should be appreciated can be a measurement of any suitable fluid or other inputted or outputted material. For example, Scale AA could be used to measure the patient's urine output instead of that parameter being inputted by the operator. Adding to the seven hundred fifty ml/hr the prescribed net loss rate of three hundred ml/hr according to the equation yields a calculated actual filtrate rate of one thousand fifty ml/hour as shown in entry 186.

The system at the beginning of the therapy as illustrated automatically determines to run filtrate pump 118 to pull one thousand fifty ml/hr to achieve the desired net loss from the patient of three hundred ml per hour based on all the other inputs and outputs shown, which can be from sources internal and external to MFT machine 20. Display 188 shows that an error would be generated if a negative ultrafiltrate rate would have been generated. Inputs 190 and 192 enable the operator to cancel displayed values or accept the values shown, respectively. It should therefore be appreciated that changing any of the amounts shown in column 176 for the various entries in rows 86 to 98 affects the calculated filtrate pump rate shown in entry 186.

Data entry layouts 194 and 196 show two possible embodiments for entering values into column 176 of GUI 60. Layout 194 is a toggling system that enables the operator to press an up arrow to increase an input or to decrease an output. Therefore, to decrease the prescribed loss shown in column 86, the operator presses the up arrow which moves the loss of three hundred towards zero. The down arrow in turn moves the loss of three hundred further away from zero. That down arrow also decreases the inputs of rows 87 to 94 towards zero, while up arrow moves the input values away from zero. When the operator is satisfied with the display of an amount, the operator presses the enter input, which enters the current value highlighted in the display above and moves the entry sequence to the next entry.

Input system 196, on the other hand, enables the operator to key in the amounts of the fluid gain or fluid loss and select whether the amount entered is a negative flow (or output) or a positive flow (or input) via the plus and minus buttons. Again, when the operator is satisfied with an entry, the operator selects the enter input to move to the next row. When all the amounts are either entered or automatically generated, the numbers displayed in entries 182 to 186 are generated. Thereafter, the operator can change values or accept the flow values via inputs 190 and 192.

The Accura™ hemodialysis/hemofiltration machine produced by the assignee of the present invention also enables the operator to use a knob to scroll through a number of selectable options and press a dedicated "enter" or "OK" button. Such a selection option is also available for use with the present invention to increase or decrease a fluid gain/loss by a set amount (e.g., in millimeter increments). Such a knob could also be used with the selectable items of FIG. 4 as well as the other selectable features (e.g., columns 172, 174 and/or 176) of FIG. 5.

System 10 enables the operator to change values over time and therefore set, for example, a desired loss rate during a first hour of therapy, a desired gain rate during the second hour of therapy and so on. The feedback via communication links 100 between the MFT machine 20 and the external input/output devices 30, 40 and 50 also enables the machine to check whether a pump is actually pumping what it has been commanded to pump. If, for example, Pump B is only inputting one hundred twenty-three ml/hour versus the one hundred twenty-five entered, system 10 automatically compensates for the loss of two ml/hour by varying the pump rate of the filtrate pump (or pump rate of the substitution pump). Such error checking can occur at regular intervals set by processor speeds or via software. System 10 in that manner becomes a highly accurate system that achieves an ultimate goal of balancing the flowrates of the numerous pumps involved with the medical fluid therapy with little operator input.

If a certain actual flowrate falls above or below the inputted flowrate to a specified degree, the information is transmitted via wiring internal to machine 20 or across the appropriate link 100 to controller 70 of machine 20, which generates an alarm notifying the operator of a flow error condition. Moreover, if the actual flowrate does not equal the entered flowrate but the disparity is not such that an alarm condition is necessary, system 10 nevertheless monitors the overall flowrate of, for example, an additive to show the operator that the patient received slightly more or less of such additive than was prescribed. The following example also highlights some of the capabilities of the present invention.

EXAMPLE

Patient XYZ's prescription has a net fluid removal rate of 300 ml/hr. XYZ's nurse enters into the MFT machine 20 that the patient is to have a prescribed-loss-rate of 300 ml/hr. Patient XYZ also has prescriptions for four administration pumps that are networked under the system 10. Patient output is measured and entered hourly. Patient XYZ's nurse enters the rates for the four pumps (e.g., Pumps A to D) directly through the MFT machine 20, or at one or more interfaces for the external devices. Patient XYZ has a urinary catheter connected to a drain bag that automatically measures the patient's urine output. Patient XYZ begins therapy and the four infusion pumps begin to administer 460 ml/hr in total.

The pumps run, nonstop, without alarm or technical problems. Patient XYZ's therapy machine 20 is instructed to give 2000 ml/hr of substitution fluid. Continuously and substantially evenly over each hour, Patient XYZ's therapy machine's filtrate pump removes 2000 ml+460 ml less any hourly amount reported by the urinary output device.

During the second hour, the prescription changes to a net gain of 100 ml/hr. The infusion administration rates are the same at 460 ml/hr. The patient's urinary output device reports there is no urine output. During the second hour, the MFT machine 20 administers the required 2000 ml/hr of substitution fluid as prescribed and removes 2360 ml of ultrafiltrate, giving Patient XYZ, a net fluid balance of +100 ml for the hour.

During the third hour, Patient XYZ experiences flow difficulties with the blood in the arterial line of the MFT machine. The machine pauses due to an extremely negative pressure in the arterial line, while the operator discovers this is due to a kink in the line. While the blood pump is paused, the MFT machine commands one of the infusion pumps to stop, because the operator had that pump set to "synchronize" with the blood pump. The operator removes the kink from the line, the blood pump restarts, and the infusion pump restarts without input from the operator. The MFT machine 20 adjusts the hourly filtrate production rate to compensate for the fluid that was not given by the infusion pump while it was paused, to meet the still prescribed net fluid change rate. A suitable appropriate message informing the operator/patient of the fluid compensation is displayed.

The first hour of the above example illustrates the ease with which internal and external flow components are entered and calculated in system 10. The second hour illustrates that the system is readily adapted to change from an overall fluid withdrawal exchange to an overall fluid netting exchange per the patient's prescribed therapy. The third hour illustrates how the system frees the operator to correct a therapy problem without having to worry about: (i) shutting down one or more pumps and (ii) making up for any downtime after the problem has been resolved.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A blood filtration system comprising:
   a blood filtration machine, including:
   a) a blood filtration machine controller housed within the blood filtration machine;
   (b) a blood pump housed integrally with the blood filtration machine, the blood pump positioned and arranged to pump blood through a blood line;
   c) a filter in fluid communication with the blood line, the filter including a dialysis solution chamber;
   d) a citrate pump housed integrally with the blood filtration machine, the citrate pump in fluid communication with the blood line and positioned and arranged to pump a citrate anticoagulant solution into the filter; and
   (e) a dialysis solution pump housed integrally with the blood filtration machine, the dialysis solution pump positioned and arranged to pump a dialysis solution into the dialysis solution chamber;
   a substitution solution fluid source; and
   a substitution solution infusion pump including a substitution solution infusion pump controller, the substitution solution infusion pump arranged to pump substitution fluid from the substitution solution fluid source into the blood line, the substitution solution infusion pump located external to the blood filtration machine, wherein the blood filtration machine controller is configured to
   automatically control the citrate pump at least in part based on a flowrate of the blood pumped by the blood pump, and
   the blood filtration machine controller is operable with the substitution solution infusion pump controller to automatically control the substitution solution infusion pump at least in part based upon an operation of the blood pump.

2. The blood filtration system of claim 1, wherein the blood filtration machine controller is further configured to cause the citrate pump to deliver a total prescribed volume of citrate.

3. The blood filtration system of claim 1, wherein the blood filtration machine controller is further configured to operate with the substitution solution infusion pump controller to perform a treatment selected from the group consisting of: continuous renal replacement therapy, dialysis, hemofiltration and any combination thereof.

4. The blood filtration system of claim 1, wherein the blood filtration machine controller automatically controls the flowrate of the citrate anticoagulant solution at least in part based upon a flow rate prescription inputted by a physician.

5. The blood filtration system of claim 1, wherein the blood filtration machine controller automatically controls the citrate pump based upon at least a blood pump rate.

6. A method of controlling a flowrate of a citrate anticoagulant solution in a renal therapy machine having a renal therapy controller, comprising:
   pumping blood through a blood circuit with a blood pump of the renal therapy machine, which is controlled by the renal therapy machine controller;
   pumping citrate anticoagulant through the blood circuit of the renal therapy machine with a citrate anticoagulant pump of the renal therapy machine, which is controlled by the renal therapy machine controller;
   pumping a substitution solution from a substitution solution source into the blood circuit with a substitution solution infusion pump located external to the renal therapy machine, the substitution solution infusion pump controlled by a substitution solution infusion pump controller; and
   causing the renal therapy machine controller to:
   (a) adjust a flowrate of the citrate anticoagulant based upon a flowrate of the blood; and
   (b) operate with the substitution solution infusion pump controller to adjust an operation of the substitution solution infusion pump based upon an operation of the blood pump.

7. The method of claim 6, which includes
   (i) pumping filtrate from the blood circuit with a filtrate pump of the renal therapy machine; and
   (ii) monitoring the blood flowrate, the citrate flowrate, the substitution solution flowrate and the filtrate flowrate to determine a net fluid loss or gain.

8. The method of claim 7, which includes comparing the net fluid loss or gain with an expected fluid loss or gain.

9. The method of claim 6, which includes adjusting the citrate anticoagulant flowrate based upon at least one of: (i) a blood flowrate signal; (ii) a substitution solution flowrate signal and (iii) a filtrate flowrate signal.

10. The method of claim 6, which includes pumping dialysate solution into a filter in communication with the blood circuit.

11. The method of claim 10, which includes adjusting the citrate anticoagulant flow rate based upon a dialysate flowrate signal.

* * * * *